(12) United States Patent
Uto et al.

(10) Patent No.: US 7,218,389 B2
(45) Date of Patent: May 15, 2007

(54) METHOD AND APPARATUS FOR INSPECTING PATTERN DEFECTS

(75) Inventors: Sachio Uto, Yokohama (JP); Minoru Yoshida, Yokohama (JP); Toshihiko Nakata, Hiratsuka (JP); Shunji Maeda, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 717 days.

(21) Appl. No.: 10/223,422

(22) Filed: Aug. 20, 2002

(65) Prior Publication Data

US 2003/0210391 A1 Nov. 13, 2003

(30) Foreign Application Priority Data

May 10, 2002 (JP) ............................. 2002-134839

(51) Int. Cl.
G02N 21/88 (2006.01)

(52) U.S. Cl. .............................. 356/237.2; 356/237.5
(58) Field of Classification Search .. 356/237.1–237.5, 356/239.1, 394; 250/548, 372, 559.44
See application file for complete search history.

(56) References Cited

U.S. PATENT DOCUMENTS

| | | | | |
|---|---|---|---|---|
| 4,812,748 A | * | 3/1989 | Brust et al. | 250/311 |
| 4,930,896 A | * | 6/1990 | Horikawa | 356/609 |
| 5,649,022 A | * | 7/1997 | Maeda et al. | 382/141 |
| 5,764,363 A | * | 6/1998 | Ooki et al. | 356/364 |
| 5,774,222 A | * | 6/1998 | Maeda et al. | 356/394 |
| 5,932,871 A | * | 8/1999 | Nakagawa et al. | 250/201.3 |
| 5,981,956 A | * | 11/1999 | Stern | 250/458.1 |
| 6,091,075 A | * | 7/2000 | Shibata et al. | 250/559.44 |
| 6,437,862 B1 | * | 8/2002 | Miyazaki et al. | 356/237.2 |
| 6,800,859 B1 | * | 10/2004 | Shishido et al. | 250/372 |

* cited by examiner

*Primary Examiner*—Hoa Q. Pham
(74) *Attorney, Agent, or Firm*—Antonelli, Terry, Stout & Kraus, LLP.

(57) ABSTRACT

A pattern defect inspection apparatus is capable of detecting defects, without being affected by non-uniform thickness of a thin film formed on a sample, even when using monochromatic light, such as a laser. The apparatus comprises a laser to illuminate a sample, coherence suppression optics to reduce laser beam coherence, a condenser to condense the laser beam onto a pupil plane of an objective lens, and a detector to detect the light reflected from a circuit pattern formed on a sample. The condenser is designed so that the intensity of light illuminating the sample under test can be partially adjusted according to the type of laser beam illumination condensed on the pupil of the objective lens. Variations in reflected light intensity caused by non-uniform film thickness on the surface of the sample are therefore reduced, and shading is minimized in the detected image to allow detecting of fine defects.

12 Claims, 10 Drawing Sheets

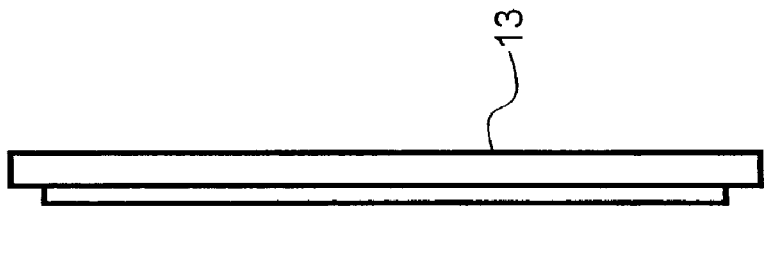
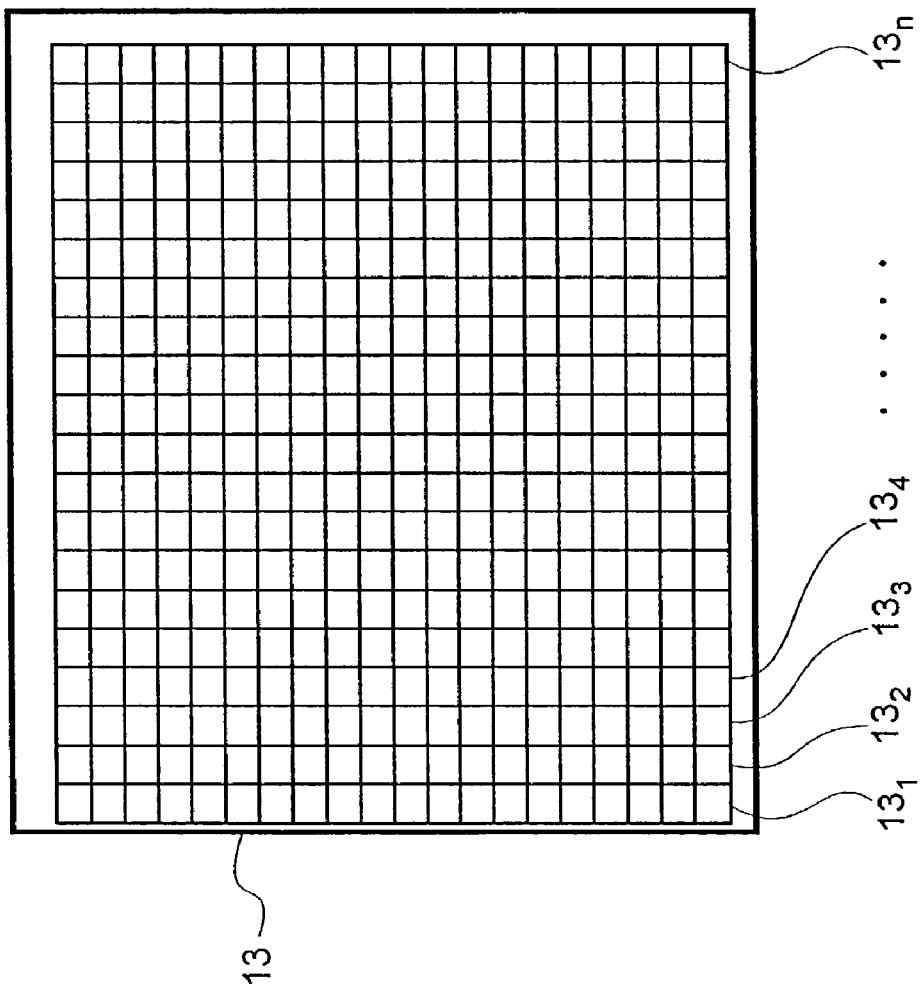

METHOD AND APPARATUS FOR INSPECTING PATTERN DEFECTS

BACKGROUND OF THE INVENTION

The present invention relates to pattern defect inspection methods and apparatus using a laser beam as illumination light, mainly for inspecting and observing defects of micro patterns or foreign matter contamination occurring in manufacturing processes for semiconductor devices and flat panel displays.

Circuit patterns tend to become finer and smaller as semiconductor devices become more highly integrated. Smaller and finer circuit patterns have spurred a demand for higher resolution when inspecting for defects of circuit patterns that have been formed on semiconductor wafers by photolithographic processes using photomasks or reticles. One technique for enhancing resolution when detecting pattern defects involves the use of illumination light on shorter wavelengths from visible light to ultraviolet light. Mercury lamps and xenon lamps, for example, have been conventionally used as illumination light sources, while only the required wavelengths from the various line spectra emitted from these lamps are optically selected and utilized.

In addition to high resolution, pattern defect inspection systems also require high intensity illumination to shorten the inspection time. Illumination from a typical light source lamp contains only a few line spectra in the ultraviolet region. A larger size lamp with higher power must be used to obtain a high intensity sufficient for high-speed pattern inspection, but this results in the problem of lower lighting efficiency. Even if high intensity illumination is obtained by utilizing a wider spectral band, there is the problem that correcting the chromatic aberration of optical systems used for pattern inspection is difficult.

Optical aligners of the type used in semiconductor device manufacturing also require the same high resolution as a pattern defect inspection apparatus, so optical aligners equipped with a KrF excimer laser that emits light at a 248 nm wavelength are mainly used. Optical aligners using an ArF laser that emits an even shorter 193 nm wavelength have also been developed. However, these excimer lasers are large in size and use fluorine gases that are harmful to the human body, so specific safety measures must be implemented.

Recently, a great deal of attention is being focused on solid-state YAG lasers as another type of ultraviolet laser. YAG lasers can generate a third harmonic (355 nm wavelength) or fourth harmonic (266 nm wavelength) by wavelength conversion when the laser beam is passed through a nonlinear optical crystal. This has led to the development of compact, easy to handle ultraviolet lasers. These compact and easy to use ultraviolet lasers are highly effective for use in a pattern inspection apparatus.

Laser beams have superior coherence, but this causes enhancement and attenuation in the light flux when they are used to illuminate a sample, and such illumination produces an interference fringe on the sample. In a pattern inspection apparatus using a laser, as disclosed in Japanese Patent JP-A No. 271213/1999, a light beam emitted from a laser light source is guided into a fly-eye lens (micro-lens array) to form a multi-spot light source. This multi-spot light source is focused so as to strike a sample under test, so that the sample is uniformly illuminated with light. The intensity of the light reflecting from the sample is then detected with a charge integration type of CCD line sensor.

The aforesaid pattern defect inspection apparatus using a laser has the following problems.

The light beam emitted from the laser is transformed into a multi-spot light source by a fly-eye lens and is focused by a condenser lens so as to illuminate the entire area of the sample under test. The incident angle of the illumination light on the surface of the sample under test is determined by the focal positions of the fly-eye lens and the condenser lens.

Multi-layered circuit patterns are fabricated on the surface of the sample (semiconductor wafer) by a semiconductor wafer process. During this process, upper layer patterns are formed on lower layer patterns with a thin film being formed between the patterns. Thus, pattern inspection is performed mainly on the upper layer patterns; however, when the surface of the sample is illuminated with light, the light reflected from the sample contains light components reflecting from the surface of the thin film and also light components reflecting from points inside of the thin film. Thus, the intensity of light reflecting from points inside of the thin film changes according to the thickness of the thin film.

Now we will discuss how the intensity of reflected light changes in cases where a thin film, such as an insulating film, is formed on the surface of a sample. A typical interference model is shown in FIG. 11. Here, the wavelength of illumination light 37 is set as λ, the incident angle of the illumination light 37 relative to a line perpendicular to the surface of the sample is θ, the refractive index of the air layer 34 is n0, the thickness and refractive index of the thin film 35 are t1 and n1, respectively, and the refractive index of the substrate 36 is n2. If the intensity of light 38 reflected from the surface of the thin film 35 is set as r01, and the intensity of light 39 reflected from the substrate 36 after passing through the thin film 35 is r12, then the composite reflected light can be defined as R. These factors can be theoretically modeled as Fresnel equations and expressed by the following equations 1 to 4.

$$X = \frac{4\pi n1 t1}{\lambda} \cos\theta \quad \text{(Eq. 1)}$$

$$r_{01} = \frac{n1 - n0}{n1 + n0} \quad \text{(Eq. 2)}$$

$$r_{12} = \frac{n2 - n1}{n2 + n1} \quad \text{(Eq. 3)}$$

$$R = \frac{r01^2 + r12^2 + 2r01 r12 \cos(\chi)}{1 + r01^2 r12^2 + 2r01 r12 \cos(\chi)} \quad \text{(Eq. 4)}$$

An example of calculated results is shown in FIG. 12, wherein the horizontal axis represents the thickness of the thin film 35 and the vertical axis represents the composite light intensity R. Changes in the composite light intensity versus the film thickness, when plotted, result in waveform 40.

However, when a laser beam is used to illuminate a sample, in order to ensure an adequate illumination sigma (s) (explained later in "Description of The Preferred Embodiments"), the laser beam must be scanned, for example, when input onto an objective lens, since lasers are point light sources. Inputting the laser beam onto the objective lens, while it is being scanned, shifts the incident angle relative to the surface of the substrate and changes the irradiance of the laser beam striking the substrate. Whether the incident light angle is large or small causes a difference in the reflected light intensity, which also varies according to the thickness of the thin film 35, as shown in FIG. 8. If the sample is inspected under such conditions, changes in reflected light intensity, due to the thickness distribution of the thin film 35, appear as changes in the brightness, causing lower detection sensitivity.

SUMMARY OF THE INVENTION

The present invention has the object of eliminating the aforesaid problems and providing a highly reliable pattern defect inspection method and apparatus, that delivers high resolution and stability for inspecting fine pattern defects using an ultraviolet laser as the light source.

A pattern defect inspection apparatus according to the present invention illuminates a semiconductor circuit pattern with ultraviolet light to detect circuit pattern defects. The apparatus is comprised of a laser light source; a coherence suppression means, located in the optical path of laser beams emitted from the laser light source, to reduce the coherence of the laser, a condenser means for condensing the laser beam passing through the coherence suppression means onto the pupil plane of an objective lens; a scanning means (incorporated in the coherence suppression means) for scanning the laser beam that has been condensed on the pupil of the objective lens by the condenser means, with any desired scan width within the pupil; and a scan speed adjustment means for making the intensity of the light reflected from the surface of the substrate uniform by changing the laser beam scan speed according to the illumination angle the relative to substrate surface, or a density adjustment means that has different transmittances according to the illumination angle relative to the substrate surface, so that the intensity of the light reflected from the surface of the sample becomes uniform. The pattern inspection apparatus of the present invention also has a detector that operates from a position above the substrate and continuously detects the light reflected from the circuit pattern, while moving the substrate at a constant speed.

These and other objects, features and advantages of the invention will be apparent from the following more particular description of preferred embodiments of the invention, as illustrated in the accompanying drawings.

BRIEF DESCRIPTION OF THE DRAWINGS

FIG. 2A is a schematic diagram showing a front view of a TDI image sensor;

FIG. 2B is a schematic diagram showing a side view of the TDI image sensor shown in FIG. 2A;

DESCRIPTION OF THE PREFERRED EMBODIMENTS

Preferred embodiments of a pattern defect inspection apparatus of the present invention will be described in detail with reference to the accompanying drawings (FIG. 1 to FIG. 13).

Figure 1:
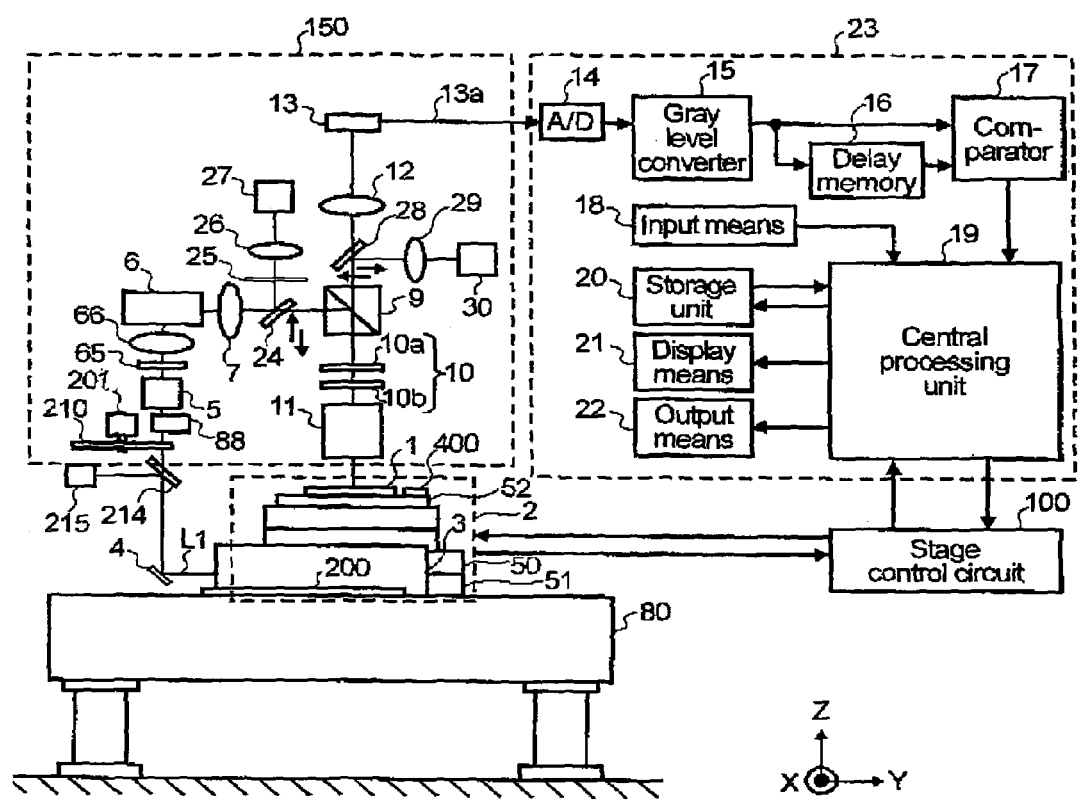
FIG. 1 is a schematic diagram showing a pattern defect inspection apparatus representing a first embodiment of the present invention.

FIG. 1 is a schematic diagram showing a pattern defect inspection apparatus representing a first embodiment of the present invention. A sample 1 comprised of a semiconductor wafer (device under test), on which there is fabricated a circuit pattern to be inspected, is placed on a stage 2. The stage 2 consists of a Z stage 52 that moves in the Z direction and rotates, a Y stage 51, an X stage 50, and a position measurement device (not shown in drawing) that measures the position of each stage. Each stage can be moved to any desired position under control from a stage controller circuit 100 that is connected to a central processing unit 19.

Component 3 in FIG. 1 is an ultraviolet laser light source (ultraviolet laser generator) that emits a far ultraviolet laser beam so as to illuminate the sample with far ultraviolet light of high intensity. A laser beam L1, that is emitted from the ultraviolet laser light source 3, is reflected from a mirror 4 and enters an objective lens 11 by way of a density adjustment device 210, beam expander 5, multi-spot forming means 65, lens 66, coherence suppression optics 6, lens 7, polarizing beam splitter 9, and polarizing optical element group 10, so that the laser beam illuminates the sample 1 on which a pattern to be inspected is formed. The beam expander 5 enlarges the ultraviolet laser beam to a certain diameter. The enlarged laser beam L1 is condensed by the lens 7 into a position near the pupil 11a of the objective lens 11, and it then strikes the sample 1.

The density adjustment device 210 adjusts the irradiance of the laser beam L1, so that the light reflecting from the sample 1 and reaching an image sensor 13 does not exceed the saturation sensitivity of the image sensor 13. This adjustment is conducted by a motor 201 that rotates the density adjustment device 210 so as to change the transmission density continuously or in steps. A mirror 214, that is installed on the optical path shown in FIG. 1, allows a portion of the laser beam L1 to diverge from the optical path, as long as the inspection is not affected, so that the output status of the laser light source 3 can be constantly monitored with a photosensitive device 215. The detected signal (not shown in the drawing) is sent to the central processing unit 19 and is monitored. Component 200 is a means for positioning the laser light source 3. If the laser light source 3 malfunctions, it should be replaced with a new laser light source 3. In this case, the positioning means 200 allows easy position alignment of the newly installed laser light source 3.

The light reflecting from the sample 1, when the sample is illuminated with the laser beam L1, is detected by the image sensor 13 by way of the objective lens 11, polarizing optical element group 10, polarizing beam splitter 9, and focusing lens 12, which are perpendicularly installed above the sample 1. The polarizing beam splitter 9 reflects the laser beam, when the polarization direction of the laser beam is parallel to the reflective surface, and it lets the laser beam pass through when the polarization direction of the laser beam is perpendicular to the reflective surface. In this embodiment, the polarizing beam splitter 9 is arranged so that the laser beam L1 undergoes total internal reflection.

The polarizing optical element group 10 functions to change the conditions of the laser beam L1 and the light reflected from the sample 1. The polarizing optical element group 10 consists of a ½ wave plate 10a and a ¼ wave plate 10b that rotate while controlled by a drive mechanism (not shown in drawing) based on the brightness of a pupil image produced by light reflecting from the pattern at the pupil position of the objective lens 11, which is viewed with a TV camera 30 via a mirror 28 and lens 29 that are arranged above the polarizing beam splitter 9. The image sensor 13 can, for example, be a charge integration type sensor (time delay integration type image sensor called TDI sensor hereafter), which is capable of detecting ultraviolet-light, and it outputs a grayscale image signal 13a according to the brightness (gray level) of the light reflecting from the pattern formed on the sample 1 under test.

The TDI sensor 13 is made up of an array of linear image sensors connected in a multistage configuration, as shown in FIG. 2. The sample 1 is first viewed with the first stage linear image sensor $13_1$ in synchronization with movement of the Y stage, that continuously moves in response to a control signal received from the central processing unit 19. The signal obtained here is transferred to the second stage linear image sensor $13_2$. Next, when the area on the sample 1, whose image was acquired with the first stage linear image sensor $13_1$ moves to the position of the second stage linear image sensor as a result of movement of the Y stage, the image in that area is again acquired, this time with the second stage linear image sensor $13_2$ and the detected signal here is added to the signal already transferred from the first stage linear image sensor $13_1$. By repeating this process for each of the subsequent stage linear image sensors up to the last stage image sensor $13_n$, the signals detected by each linear image sensor stage are all accumulated and output.

In the above-described apparatus, the central processing unit 19 issues an instruction to the stage control circuit 100. On receiving the instruction, the Y stage 51 moves in the Y direction at a constant speed with the sample mounted thereon. Meanwhile, the Z direction shift of the sample 1 is detected by a focus detector system (not shown in drawing) to control the Z stage 52 so that the surface of the sample 1 is always at the focusing position of the objective lens 11.

Brightness information (grayscale image signal) on the pattern formed on the sample 1 under test is detected by the image sensor (TDI sensor) 13 in synchronization with the movement of the Y stage 51, which continuously moves according to position data for the Y stage 51, that is monitored using a Y stage position detector (not shown in drawing). The grayscale image signal 13a, that is obtained with the image sensor 13, is input to a signal processing circuit 23 to inspect and find pattern defects in the sample 1.

The signal processing circuit 23 is comprised of an A/D converter 14, a gray level converter 15, delay memory 16, comparator 17, and central processing unit 19. The A/D converter 14 converts the grayscale image signal 13a, that has been obtained with the image sensor 13, into a digital signal. A calibration plate 400, that is provided on the stage, is used to set the focusing position of the above-mentioned focal position detector system, so that the focal position can be automatically determined at any desired Z position on the surface of the sample 1 by offset adjustment. Here, the A/D converter 14 can also be installed in the detector optical system 150, at a location immediately after (downstream) the image sensor (TDI sensor) 13, instead of being installed in the signal processing circuit 23. In this case, a digital image signal is transferred from the detector optical system 150 to the signal processing circuit 23.

The gray level converter 15 consists, for example, of an 8 bit gray level converter, and it performs gray level conversion on the digital image signal transferred from the AND converter 14, as described in Japanese Patent JP-A No. 320294/1996. The gray level converter 15 performs this conversion using logarithmic, exponential and polynomial expressions to correct shading or uneven brightness on the image caused by laser beam interference with the thin film formed on the sample 1 under test (such as thin films formed on a semiconductor wafer during a wafer process). The delay memory 16 stores the image signal transferred from the gray level converter 15, within a period of the scan width of the image sensor 13, so as to produce a delay equal to one cell or one chip or one shot comprising the sample (semiconductor wafer).

The comparator 17 compares the image signal transferred from the gray level converter 15 with the image signal obtained through the delay memory 16, in order to detect mismatches between them as defects. In other words, the comparator 17 compares the detected image with an image transferred from the delay memory 16 that was obtained with a delay equal to the cell pitch, etc.

The central processing unit 19 creates defect inspection data, based on the inspection results that were produced by the comparator 17, and also based on the arrangement coordinate data on the sample 1 (semiconductor wafer). This data is obtainable from circuit design information and should be entered in advance from an input means 18, consisting of a keyboard, storage medium, network, etc. This defect inspection data is stored in the storage unit 20, and it can be displayed on a display means 21 as needed, or it can be output to an output means 22 for observing the locations of defects on other review devices.

Figure 3:
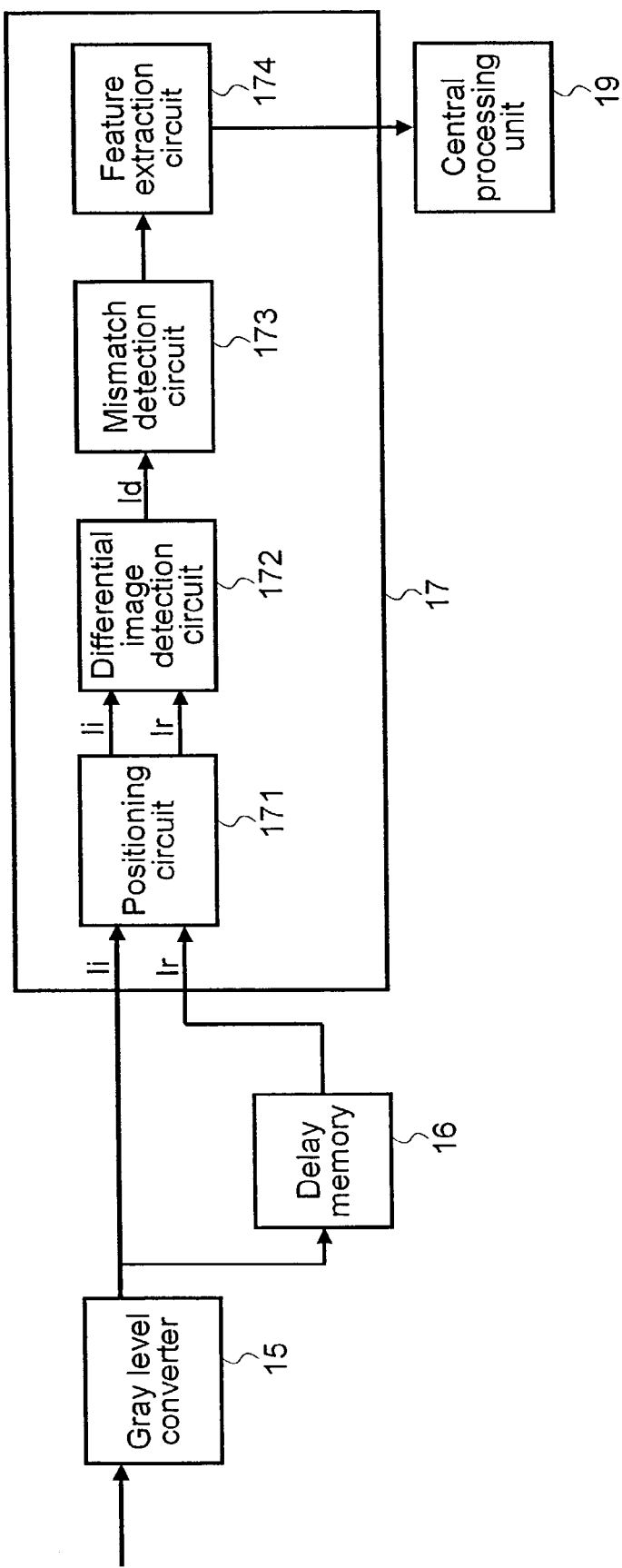
FIG. 3 is a block diagram of the comparator 17 shown in FIG. 1.

The comparator 17 can be configured like that disclosed in Japanese Patent JP-A No. 212708/1986. The comparator 17, as shown in FIG. 3, for example, consists of a positioning circuit 171, that aligns the positions of the comparison image Ii that has been transferred from the gray level converter 15 and the reference image Ir that has been transferred from the delay memory 16; a differential image detection circuit 172, that detects a differential image Id that represents the difference between the comparison image Ii and the reference image Ir, that were aligned with each other by the positioning circuit 171; a mismatch detection circuit 173, that converts the differential image Id that has been detected by the differential image detection circuit 172 into a binary image by setting a threshold level; and a feature extraction circuit 174, that extracts information about the area, length and coordinates from the binary output transferred from the mismatch detection circuit 173.

In pattern defect inspection, shorter wavelengths are essential to obtain a higher resolution, and higher intensity illumination is also required to improve the inspection speed. Discharge lamps, such as mercury-xenon lamps, therefore, are widely used as illumination light sources for this purpose. Since these discharge lamps produce high intensity in the visible region, line spectra in the visible region are mainly utilized to obtain higher intensity illumination. Line spectra in the ultraviolet to deep ultraviolet region are only a few percent of those in the visible region, so that a high-power lamp must be used to obtain the required ultraviolet intensity. Moreover, the optical system must be separated from the light source to prevent adverse effects from heat emanating from the light source, that cause the problem of overheating when the space is limited. In view of these problems, the present invention uses an ultraviolet laser, or far ultraviolet (deep ultraviolet or DUV) laser, that emits a short-wavelength light beam. The ultraviolet laser mentioned with reference to the present invention is a laser that emits light in a wavelength range from 100 nm to 400 nm, and a DUV laser is a laser that emits light in a wavelength range from 100 nm to 314 nm.

Lasers are well known as coherent light sources (having coherence), so that, when a laser beam illuminates the sample 1 under test, speckle noise (interference fringes) occurs, causing trouble during pattern defect inspection. Because of this problem, the present invention uses the coherence suppression optics 6 to spatially reduce the coherence of the laser beams and thereby minimize speckle noise.

Figure 4:
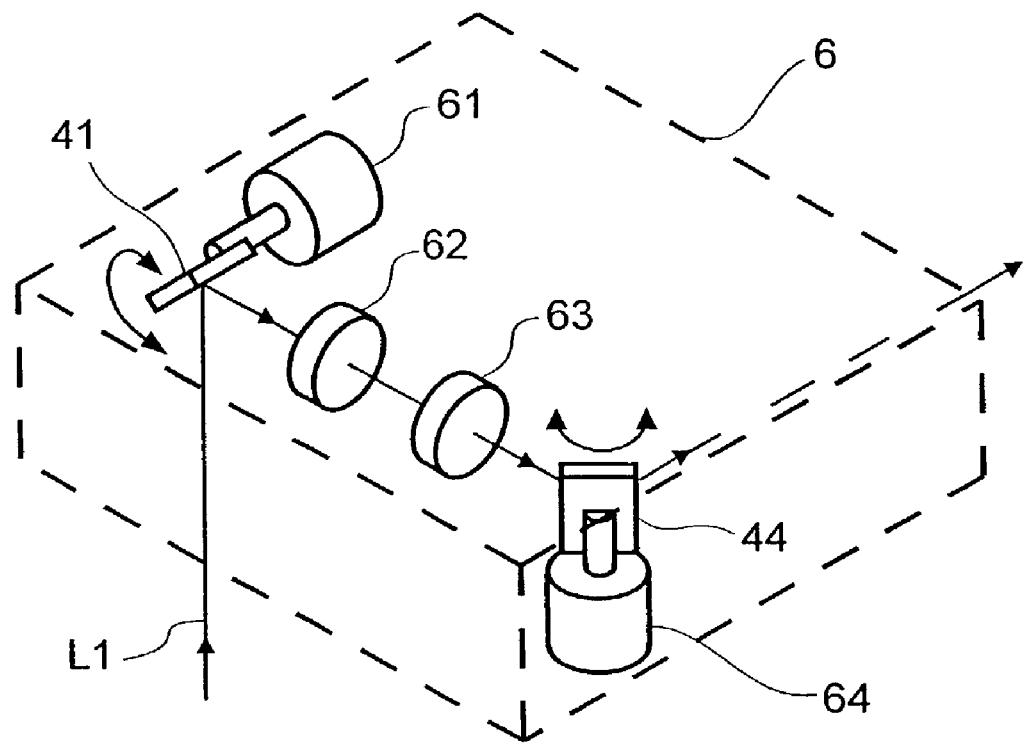
FIG. 4 is a simplified pictorial diagram of the coherence suppression optics of the present invention shown in FIG. 1.

FIG. 4 is a simplified pictorial drawing of one example of the coherence suppression optics 6 of the present invention. In accordance with the present invention, two scanning mirrors 41 and 44, that are installed on the optical path, are used to reduce the coherence by scanning the laser beam L1 on the pupil of the objective lens 11 two-dimensionally. Before the laser beam L1 is input to the coherence suppression optics 6, the laser beam L1 is enlarged to a certain diameter by the beam expander 5, and this enlarged beam is then input into the multi-spot forming device 65, that forms multiple laser spots (a multi-spot image) at the focal position of the multi-spot forming device 65.

Figure 5A:
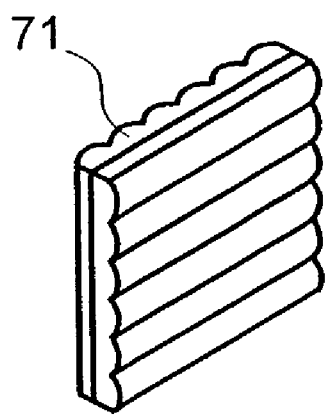
FIG. 5A is a simplified diagram of the lens array used in the multi-spot forming means shown in FIG. 1.
Figure 5B:
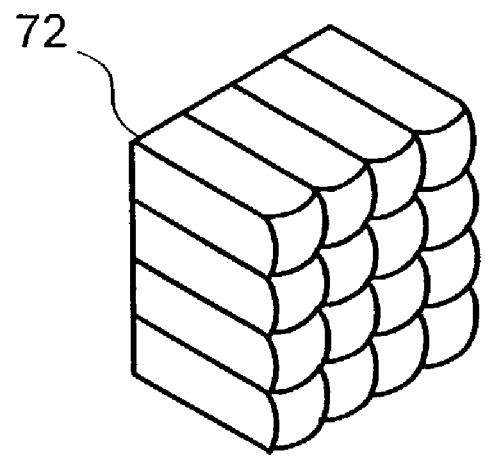
FIG. 5B is a simplified diagram of another lens array used in the multi-spot forming means shown in FIG. 1.

As an example of the multi-spot forming device 65, a cylindrical lens array 71, that is installed at a right angle, can be used, as shown in FIG. 5A, or a rod lens array 72, consisting of micro-lenses stacked in two dimensions, can be used, as shown in FIG. 5B.

The laser beam L1, that is emitted from the multi-spot forming device 65, is condensed onto the pupil 11a of the objective lens 11 (see FIG. 7A and FIG. 7B) by way of a lens 66, lenses 62 and 63 in the coherence suppression optics 6, lens 7, and polarizing beam splitter 9. The multi-spot forming device 65 has a focal position conjugate with the pupil 11a of the objective lens 11, while the reflective surfaces of the scanning mirrors 41 and 44 are conjugate with the surface of the sample 1. The scanning mirrors 41 and 44 are respectively attached to motors 61 and 64 that rotate back and forth in response to input of a drive signal (not shown in the drawing), for example, a sine wave or triangular wave signal, generated in the central processing unit 19, so that the laser beam spots are two-dimensionally scanned on the objective lens pupil 11a. The drive signal (such as a sine wave or triangular wave signal) for the motors 61 and 64 can be generated by using the encoder pulses of a position detector (not shown in drawing) that controls the stage position. This drive signal waveform is shifted every one cycle in synchronization with the integration time of the image sensor 13. The scan width for the laser beam spots can be adjusted by changing the amplitude of the drive signal waveform.

Figure 6A:
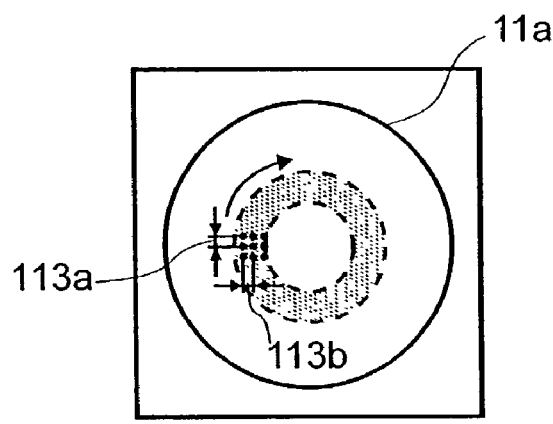
FIG. 6A is a diagram which shows how multiple laser spots are formed and scanned by the coherence suppression optics of FIG. 4 in accordance with the present invention.
Figure 6B:
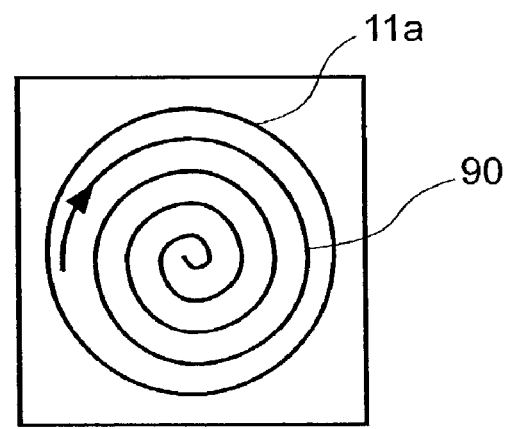
FIG. 6B is a diagram showing a helical scan pattern of laser spots produced by the coherence suppression optics of FIG. 4 in accordance with the present invention.

In the present embodiment, by splitting the laser beam L1, with the use of a mirror 24 interposed in the optical path, the track of the laser beam scanned on the objective lens pupil 11a can be projected and observed on a screen 25, that is arranged in the conjugate position of the objective lens pupil ha. The screen 25 has a phosphorescent property and emits light when irradiated with ultraviolet rays, so that an invisible ultraviolet laser beam can be seen. FIG. 6A and FIG. 6B show an example of laser beam scan tracks formed on the screen 25, as viewed with a TV camera 27 via a lens 26.

Whether the image detected by the image sensor 13 is clear or not depends on the illumination conditions. In the present embodiment, illumination s on the pupil 11a of the objective lens 11 can be adjusted by controlling the scan width of the mirrors 41 and 44, and the drive signal to be input to the motors 61 and 64 is controlled so that the laser scan cycle on the pupil 11a of the objective lens 11 is synchronized with the integration time of the image sensor 13. The illumination sigma (s) mentioned here is the ratio of the multi-spot illumination area to the objective lens pupil size. If s=1, this means that the multi-spot image fills the entire pupil of the objective, while the light beam is scanned within a certain duration of time. The magnification of the multi-spot image formed on the pupil of the objective lens can be determined by the focal length between the lens 66 and lens 7. In other words, to obtain the same illumination s when using the same number of spots, scanning with a larger multi-spot image will make it possible to reduce the number of scans, rather than trying to scan with a smaller multi-spot image.

Figure 7A:
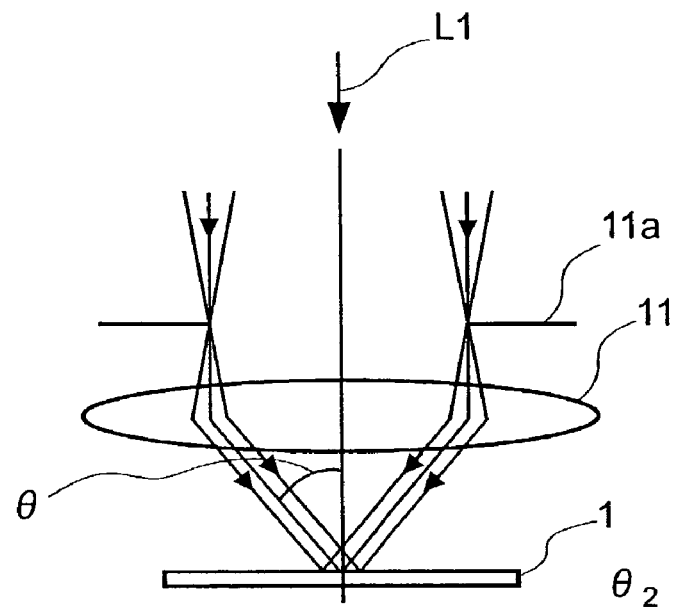
FIG. 7A is a diagram which shows laser beam scanning onto an objective lens in accordance with the present invention.
Figure 7B:
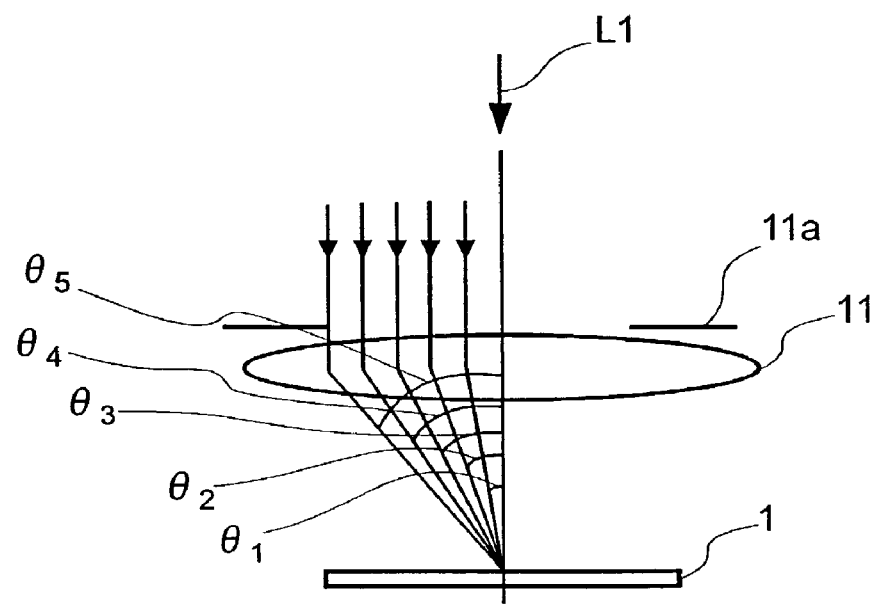
FIG. 7B is a diagram which also shows laser beam scanning onto an objective lens in accordance with the present invention.
Figure 8:
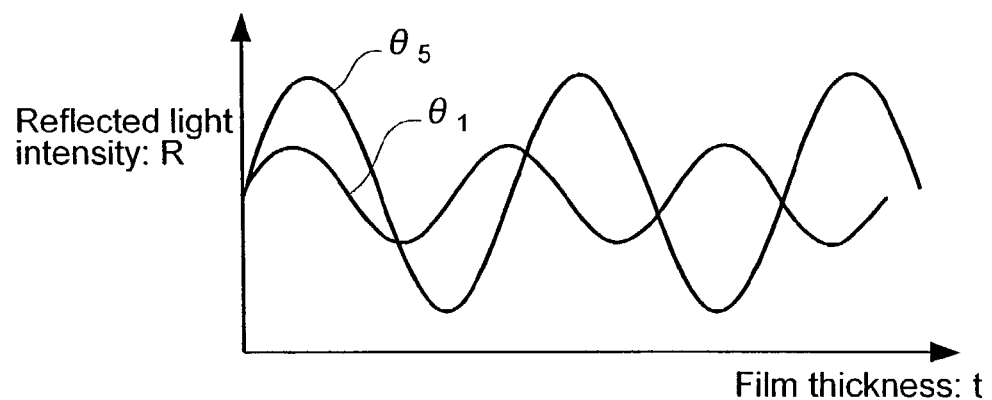
FIG. 8 is a graph that shows thin film interference that varies with the incident angle of illumination light.

To improve the pattern inspection speed, the image sensor 13 should cover a wide area on the sample 1. At the same time, the illumination width should also be widened. As shown in FIG. 7A, a larger illumination width can be obtained on the sample as the NA (numerical aperture) of the laser beam incident on the pupil 11a of the objective lens 11 is made larger and the laser beam is condensed into a smaller spot. However, this also widens the intervals between each laser spot (113a and 113b shown in FIG. 6A). In order to fill the entire pupil 11a of the objective lens 11 with multi-spot scanning (for example, circular scan on the pupil), while using this optical configuration, the diameter of the scanning circle should gradually be made smaller for each rotational scan according to the shape of the multi-spot image (laser spot diameter), so that the scanning pattern draws a helical track, as shown in FIG. 6B. In this case, the laser beam L1 illuminates the same position on the surface of the sample 1, while changing the incident angle θ formed by the incident direction of the laser beam L1 and a line mounted to the surface of the sample 1. This means that the larger the incident angle θ, the longer will be the distance of the circular scanning, while the smaller the incident angle θ is, the shorter will be the distance of the circular scanning. Therefore, the laser beam irradiation time per unit area on the sample 1 differs according to the incident angle of the laser beam L1. The reflected light intensity distributions at different incident angles are plotted versus the thickness of the thin film 35 on the surface of the sample 1, as shown in FIG. 8. From this, it is seen that the non-uniformity of the thin film formed on the pattern surface of the sample 1 causes uneven brightness or shading on the image. This non-uniform brightness or shading causes misdetection, since normal sections on the circuit pattern may be viewed as defects, when compared with the reference image transferred from the delay memory 16.

Figure 9A:
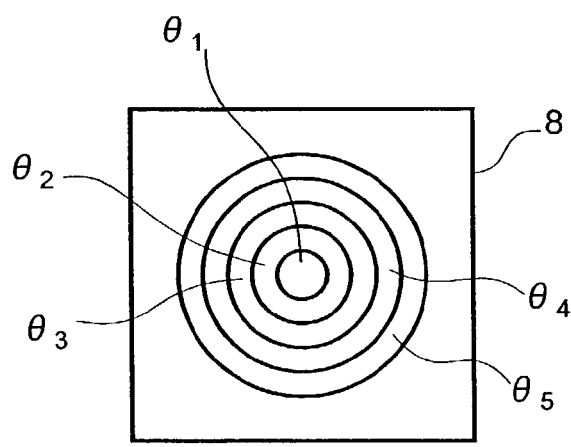
FIG. 9A is a simplified diagram of the density adjustment means of the present invention for controlling the transmittance of illumination light.
Figure 9B:
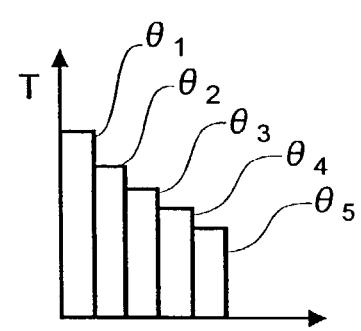
FIG. 9B is a diagram which shows transmittance of illumination light that varies with the incident angle.
Figure 10:
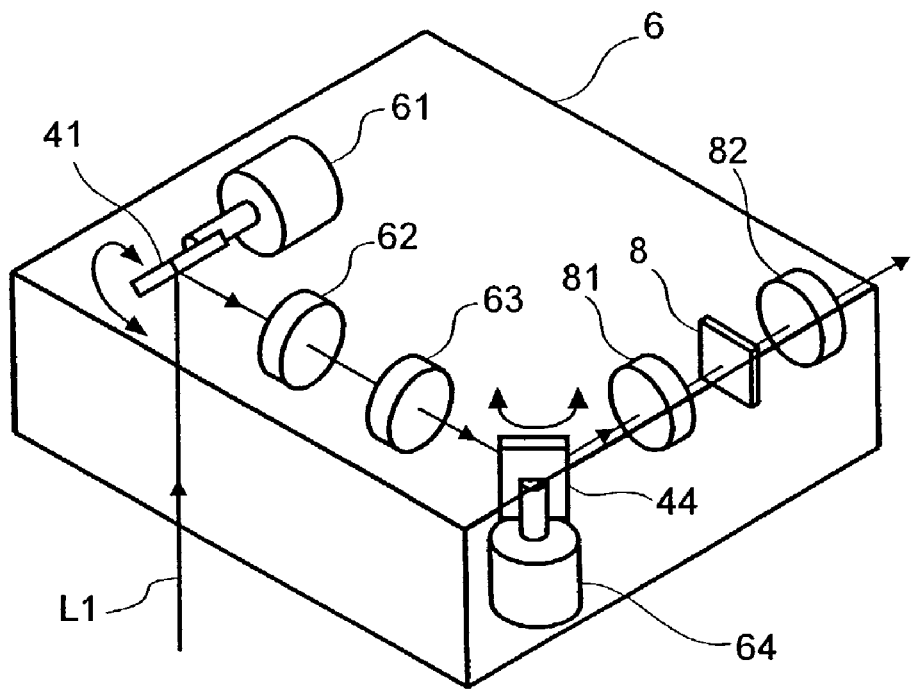
FIG. 10 is a simplified pictorial diagram of the optics used in accordance with the present invention for controlling the transmittance of illumination light.
Figure 11:
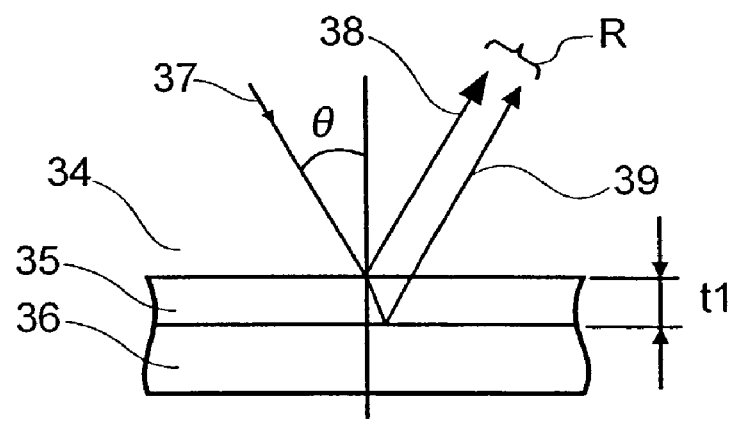
FIG. 11 is a diagrammatic cross sectional view of a semiconductor substrate showing thin film interference that varies with the incident angle of illumination light.
Figure 12:
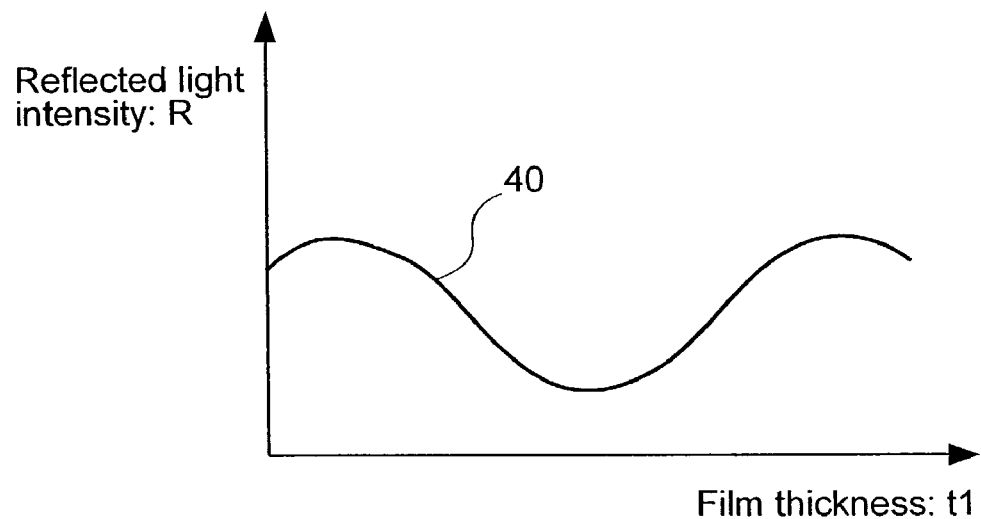
FIG. 12 is a graph which shows interference intensity as a function of the thin film thickness.

To solve the aforementioned problem, the first embodiment of the present invention uses a density filter 8 that changes the transmittance according to the incident angle θ of the laser beam, as shown in FIG. 9A and FIG. 9B. This density filter 8 is arranged on the optical path so that the reflected light intensity to be detected becomes uniform. The density filter 8, for example, can be interposed between the lenses 81 and 82 of the coherence suppression optics 6, as shown in FIG. 10, and arranged at a position conjugate with the pupil 11a of the objective lens 11 after (downstream) the rotational scanning mirrors 41 and 44. The transmittance ratio of the density filter 8 can be experimentally obtained.

As a second embodiment of the present invention, the laser beam L1 may be input into the objective lens, while changing the irradiance of the laser beam L1 according to the scan track of the laser beam L1 on the pupil 11a of the objective lens 11. More specifically, the scan track of the laser beam L1 is detected in advance, by way of the screen 25, lens 26 and TV camera 27, so as to measure the positional relation with the drive signal fed to the motors 61 and 64 that scan the laser beam L1. The irradiance of the laser beam L1 is then controlled at high speeds by using a density adjustment means 88, as shown in FIG. 1. An optical element, such as an A/O modulator, can be used as the density adjustment means 88.

In accordance with the present invention, the cycle of the two-dimensional scan of the laser beam L1 is synchronized with the image acquisition cycle of the image sensor 13, and the incident angle θ of the light beam is also sequentially changed according to each cycle. This allows image acquisition, while reducing the adverse effects resulting from the film thickness distribution of an optically transparent film formed on the surface of the sample 1.

In accordance with the present invention, when an image of a position on the sample 1 is acquired with the first stage linear image sensor $13_1$ of the TDI sensor 13 (see FIG. 2), the laser beam L1, that illuminates the sample 1, is scanned in two dimensions on the pupil 11a of the objective lens 11, and it strikes the sample 1 at an incident angle of $θ_1$. When the sample 1 next moves to a point where an image of the same position on the sample 1 is acquired by the second stage linear image sensor $13_2$ of the TDI sensor 13, the laser beam L1, that illuminates the sample 1, is also scanned in two dimensions on the pupil 11a of the objective lens 11, and it strikes the sample 1 at an incident angle of $θ_2$. The image signal of a position on the sample 1, that was detected with the first stage linear image sensor $13_1$ is added to the image signal of the same position on the sample 1 that was detected with the second stage linear image sensor $13_2$, and this added signal is transferred from the second stage linear image sensor $13_2$ to the third stage linear image sensor $13_3$. An image signal of the same position on the sample 1 is again acquired with the third stage linear image sensor $13_3$ while the laser beam L1 strikes the sample 1 at an incident angle of θ3. This image signal is further added to the signal already transferred from the second stage image sensor $13_2$, and the added signal is then transferred to the fourth stage linear image sensor $13_4$.

In this way, each linear image sensor stage of the TDI sensor 13 detects an image of the same position on the sample 1 on which the laser beam L1 falls at a different incident angle θ, and it outputs the sum of the signals detected by all the linear image sensors. In other words, the TDI sensor 13 outputs an average image signal containing multiple images of the same position on the sample 1, that were acquired with the laser beam L1 falling on the sample 1 at different incident angles θ and summed together. This reduces adverse effects from the film thickness distribution of an optically transparent film formed on the surface of the sample 1, allowing accurate detection of pattern defects, while maintaining high sensitivity.

Figure 5C:
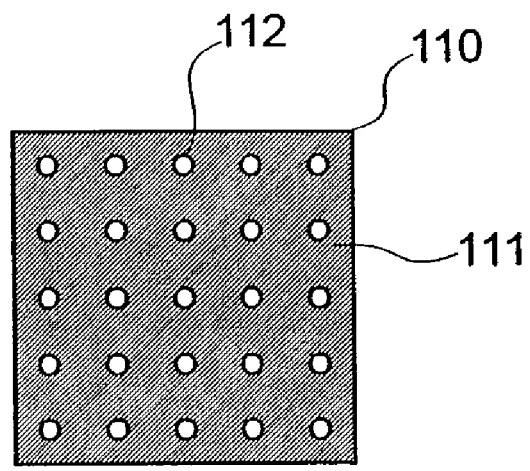
FIG. 5C is a diagram which shows an image of multiple light spots produced by the multi-spot forming means shown in FIG. 1.
Figure 13:
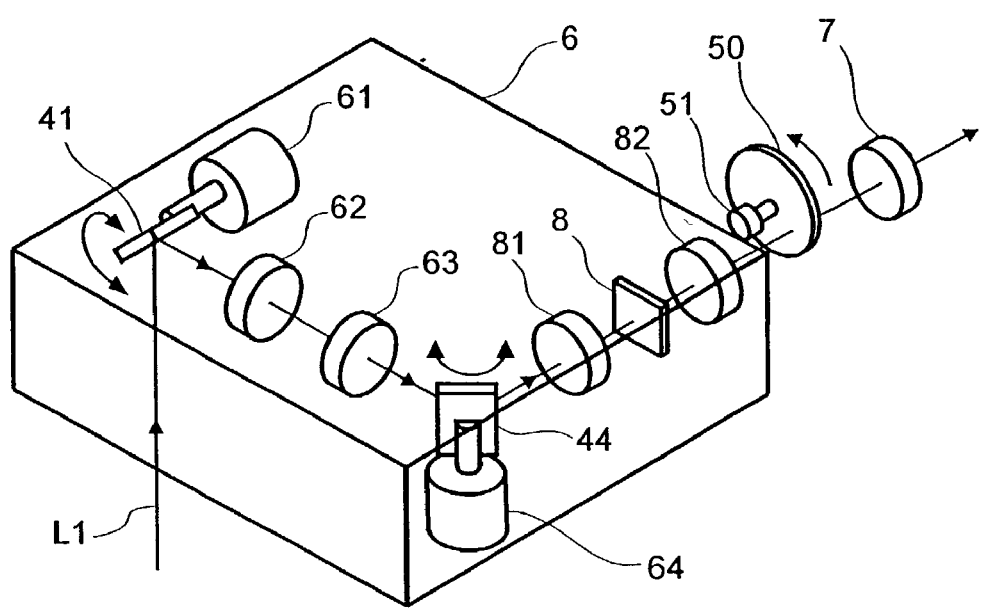
FIG. 13 is a simplified pictorial diagram of another embodiment of coherence suppression optics of the present invention.

Next, another embodiment of the coherence suppression optics 6 will be described with reference to FIG. 13. In this embodiment, a circular diffuser plate (rotating optical element) 50 is provided after (downstream) the scanning mirrors 4i and 44 (also shown in FIG. 4), along with a motor 5i that rotates the diffuser plate 50 at high speeds. More specifically, the diffuser plate 50, whose surface is machined to have the proper roughness, is arranged near the focal position of the lens 82 (or lens 7), and the motor 51 rotates the diffuser plate 50 so that the coherency of the ultraviolet laser spot is made lower, to some extent, in comparison to a laser without a diffuser plate, when it is condensed and scanned on the pupil 11a of the objective lens 11. Therefore, the spatial coherence of the laser beam is reduced. In addition, by installing a mask 110 (FIG. 5C) at the focal position of the multi-spot forming device, a better-shaped light spot image can be obtained on the pupil 11a of the objective lens 11. As shown in FIG. 5C, the mask 110 consists of light transmitting portions 112, provided at the position corresponding to a multi-spot image, and a light-shielded area 111, where a multi-spot image is not projected. Using this mask can also reduce the adverse effects from interference, even when the laser beam L1 having a high coherence is used, allowing pattern defects to be detected with high sensitivity.

A method of inspecting a circuit pattern formed on a semiconductor wafer to detect defects will be described next with reference to an inspection apparatus equipped with the devices mentioned in the foregoing description of the present invention.

First of all, a wafer 1, that represents a sample to be inspected, is placed on the Z stage 52 of the stage 2 and is positioned correctly. Next, the stage 2 holding the wafer 1 moves in the Y-axis direction at a constant speed, when the stage control circuit 100 receives a signal to drive the Y stage 51 from a stage position sensor (not shown in drawing).

Meanwhile, a far ultraviolet laser beam is emitted from the ultraviolet laser light source 3, and the laser beam diameter is enlarged by the beam expander 5. The laser beam is then transformed into multiple spots when it passes through the multi-spot forming device 65.

The laser beam that has been transformed into multiple spots enters the coherence suppression optics 6 and is output while being scanned by the scanning mirrors 41 and 44 in two intersecting axial directions. The laser beam, that has been emitted from the coherence suppression optics 6, has its optical path shifted at the polarizing beam splitter 9, passes through the polarizing optical element group 10, where the polarization state of the beam is adjusted, and enters the objective lens 11. The objective lens 11 condenses the laser beam onto the surface of the wafer 1.

The laser beam, that is scanned in two intersecting axial directions by the scanning mirrors 41 and 44 in the coherence suppression optics 6, is scanned along a circle on the pupil plane 11a of the objective lens 11. The wafer 1, while being illuminated at the same time, moves at a constant speed in the Y axis direction, while the incident angle of the beam is sequentially changed relative to the normal line direction on the surface of wafer 1 at each circular scan.

The reflected light from the wafer 1, that is illuminated with the laser beam, is condensed by the objective lens 11 so as to pass through the polarizing optical element group 10, and it reaches the image sensor 13. An image of the wafer 1 is therefore focused on the image sensor 13.

As mentioned above, the image sensor 13 is a time delay integration image sensor that is made up of a number of linear image sensors connected in a multiple stage array. The image signals detected at each stage of the linear image sensors are sequentially transferred to the linear image sensor of the next stage and accumulated. This transfer timing is synchronized with the movement of the Y stage 51, that is constantly detected with the stage position sensor.

A grayscale image signal 13a of the wafer 1, that is acquired with the image sensor 13, is converted into a digital signal by the A/D converter 14. Shading or uneven brightness on the image, that has been caused by interference of the laser beam with the thin film formed on the wafer 1 under test, is corrected with the gray level converter 15. The signal processed by the gray level converter 15 is divided into two signals. One is stored in the delay memory, and the other is input to the comparator 17.

In the comparator 17, the comparison image Ii, that has been transferred from the gray level converter 15, and the reference image Ir, that was detected in the previous step (adjacent chip or adjacent pattern) and stored in the delay memory 16, are both input to the positioning circuit 171. The positioning circuit 171 finds the positional shift (deviation) between the comparison image Ii and the reference image Ir and corrects this shift.

The positioning circuit 171 outputs the comparison image Ii and the reference image Ir after correcting their mutual positional shift (deviation) and inputs them to the differential image detection circuit 172, where a differential image Id representing the difference between the two images is obtained. The differential image Id obtained here is sent to the mismatch detection circuit 173, and it is compared with a preset threshold level. Portions higher than this threshold level are detected as defects. The information about the defects is then sent to the feature extraction circuit 174.

The feature extraction circuit 174 extracts information about the area, length and coordinates of the defects detected by the mismatch detection circuit 173, and it sends the information to the central processing unit 19. The central processing unit 19 stores the information about the defects in the memory unit 20, and it also displays this information on the screen of the display means 21. Though not shown in FIG. 1 and FIG. 3, the comparison image Ii, that was transferred from the gray level converter 15 and whose positional shift was corrected by the positioning circuit 171, is also input to the central processing unit 19 and stored in the memory unit 20, or displayed as an image containing defects on the screen of the display means 21, as needed. Information about the defects stored in the memory unit 20 can be transferred via communication lines from the output means to other devices, such as review or evaluation devices used to observe a detailed view of the defects.

As described above, the present invention makes it possible to average the light intensity reflected from the sample, regardless of the laser beam incident angle, by changing the incident angle of the laser beam that illuminates the sample. This reduces variations in the reflected light intensity caused by non-uniform thickness of a thin film formed on the surface of the sample and minimizes shading or uneven brightness on the detected image, thereby allowing accurate detection of fine defects. Inspection can also be performed with high sensitivity, because variations or fluctuations in light intensity during scanning, due to non-uniform thin-film thickness among chips, that occur depending on sample positions can be cancelled out.

The present invention is also effective in process control when sudden fluctuations in light intensity are detected during inspection.

The invention may be embodied in other specific forms without departing from the spirit or essential characteristics thereof. The present invention is therefore to be considered in all respects as illustrated by the appended claims rather than by the foregoing description, and all changes which come within the meaning and range of equivalency of the claims are therefore intended to be embraced therein.

What is claimed is:

1. A method of inspecting pattern defects, comprising:
   emitting a laser beam from an ultraviolet laser light source or a deep ultraviolet laser light source;
   illuminating said emitted laser beam on the surface of a sample after reducing coherence of said laser beam;
   acquiring an image of the illuminated sample by detecting light with a time delay integration sensor and said light is reflected from said sample by said illuminating and passed through a filter; and
   processing the acquired image to find pattern defects on the surface of the sample,
   wherein said laser beam illuminating said surface of said sample is so controlled that said light reflected from said sample is uniform in intensity, and,
   wherein the laser beam emitted from said ultraviolet laser light source or said deep ultraviolet laser light source is scanned in two dimensions on a pupil plane of an objective lens.

2. The method of inspecting pattern defects according to claim 1, comprising:
   holding the sample on a table that is moved along at least one direction; and
   acquiring an image of the sample illuminated by the laser beam by said time delay integration sensor synchronized with movement of the table.

3. The method of inspecting pattern defects according to claim 1, comprising changing the irradiance of the laser beam being illuminated on the surface of the sample, according to an incident angle thereof relative to the normal line direction on the surface of the sample.

4. A method of inspecting pattern defects, comprising:
   emitting a light beam from a light source;
   illuminating said light beam on the surface of a sample through an object lens and said sample is held on a table that is continuously moving along at least one axis direction, while repeatedly changing a condition of illuminating;
   acquiring an image of the illuminated sample by a time delay integration sensor in synchronous with movement of said table; and
   processing the acquired image to find pattern defects on the surface of the sample,
   wherein said condition of said illuminating is so controlled that an output from said time delay integration sensor is average image signal to reduce an influence of a film thickness distribution of said optically transparent thin film formed on said sample; and, wherein said condition of said illuminating is controlled to change an incident angle of said light beam to a normal line direction to said surface while scanning said light beam on a pupil plane of said object lens.

5. The method of inspecting pattern defects according to claim 4, wherein the light source is an ultraviolet laser light source or a deep ultraviolet laser light source.

6. A method of inspecting pattern defects, comprising:
illuminating a light beam emitted from a light source on the surface of a sample held on a table that is moving continuously, while chancing a condition of said illuminating;
acquiring an image of the illuminated sample by detecting light from said illuminated sample with a time delay integration sensor, in synchronization with the continuous movement of the table; and
processing the acquired image to find pattern defects on the surface of the sample,
wherein said condition of said illumination is so controlled that an output from said time delay integration sensor is average image signal to reduce an influence of a film thickness distribution of an optically transparent thin film formed on said sample, and,
wherein said condition of said illuminating is controlled to change an incident angle of said light beam to a normal line direction to said surface while scanning said light beam on a pupil plane of said object lens.

7. The method of inspecting pattern defects according to claim 6, wherein said light beam illuminating said surface of said sample is so controlled that said light reflected from said sample is uniform in intensity.

8. The method of inspecting pattern defects according to claim 6, wherein the light source is an ultraviolet laser light source or deep ultraviolet laser light source.

9. An apparatus for inspecting pattern defects, comprising:
a light source;
a table on which a sample is placed, said table being capable of moving along at least one plane;
an objective lens that condenses and irradiates a beam emitted from the light source onto a sample placed on the table;
a scanning device that scans the laser beam in two dimensions on the pupil plane of the objective lens and also irradiates the laser beam, while scanning it in two dimensions, onto the surface of the sample, while changing the incident angle thereof relative to the normal line direction on the surface of the sample;
an imaging device that acquires an image of the sample with a time delay integration sensor in synchronous with the movement of said table;
a pattern defect detector that finds pattern defects of the sample by processing an image of the sample acquired with the imaging device when the sample is illuminated with the beam; and
a controller which controls a condition of said irradiating a laser beam onto said sample so as to an output from said time delay integration sensor be average image single which reduces an influence of a film thickness distribution of said optically transparent thin film.

10. The apparatus for inspecting pattern defects according to claim 9, wherein the light source emits an ultraviolet laser beam or a deep ultraviolet laser beam.

11. The apparatus for inspecting pattern defects according to claim 9, comprising a beam forming means that transforms a beam emitted from the light source into a number of light spots.

12. The apparatus for inspecting pattern defects according to claim 9, comprising an irradiance adjustment device that changes the irradiance of the light beam illuminating the surface of the sample according to an incident angle thereof relative to the normal line direction on the surface of the sample.

* * * * *